United States Patent
Fernandez et al.

(10) Patent No.: US 12,376,788 B2
(45) Date of Patent: Aug. 5, 2025

(54) SMART MATTRESS TOPPER SYSTEM AND ASSOCIATED METHOD

(71) Applicant: REZET TECHNOLOGIES, INC., Beaverton, OR (US)

(72) Inventors: Javier Fernandez, Beaverton, OR (US); Oscar Valdemoros, Beaverton, OR (US)

(73) Assignee: REZET TECHNOLOGIES, INC., Beaverton, OR (US)

( * ) Notice: Subject to any disclaimer, the term of this patent is extended or adjusted under 35 U.S.C. 154(b) by 484 days.

(21) Appl. No.: 17/829,774

(22) Filed: Jun. 1, 2022

(65) Prior Publication Data

US 2023/0389714 A1    Dec. 7, 2023

(51) Int. Cl.
*A61B 5/00* (2006.01)
*A47C 27/08* (2006.01)
*A61B 5/024* (2006.01)
*G05B 13/02* (2006.01)
*G05B 13/04* (2006.01)
*G16H 50/30* (2018.01)

(52) U.S. Cl.
CPC .......... *A61B 5/4815* (2013.01); *A47C 27/082* (2013.01); *A47C 27/083* (2013.01); *A61B 5/0022* (2013.01); *A61B 5/02405* (2013.01); *G05B 13/0265* (2013.01); *G05B 13/048* (2013.01); *G16H 50/30* (2018.01)

(58) Field of Classification Search
CPC ..... A47C 21/04; A47C 21/044; A47C 27/082; A47C 27/083; A61B 5/0022; A61B 5/4806; A61B 5/4812; A61B 5/4815; A61B 5/74; A61B 5/7405; A61B 5/742; A61B 5/7455; G05B 13/0265; G05B 13/048
USPC ........................................................ 700/301
See application file for complete search history.

(56) References Cited

U.S. PATENT DOCUMENTS

| | | | |
|---|---|---|---|
| 10,413,233 B2 * | 9/2019 | Meriheinä | A61B 5/091 |
| 10,925,410 B2 * | 2/2021 | Hsu | A61B 5/445 |
| 11,241,100 B2 * | 2/2022 | Chapin | A47C 21/044 |
| 11,937,905 B2 * | 3/2024 | Singleton | A61B 5/0022 |
| 12,156,723 B2 * | 12/2024 | Hatch | A61B 5/412 |
| 12,165,771 B2 * | 12/2024 | Kyyrö | G16H 40/63 |

(Continued)

FOREIGN PATENT DOCUMENTS

| | | | | |
|---|---|---|---|---|
| CN | 106039585 A | * | 10/2016 | A47C 27/15 |
| CN | 107657748 A | * | 2/2018 | A47C 21/04 |

(Continued)

*Primary Examiner* — Crystal J Barnes-Bullock
(74) *Attorney, Agent, or Firm* — LUCAS & MERCANTI, LLP

(57) ABSTRACT

Smart mattress topper system and method that uses a smart mattress topper connected to the Internet (IoT), which includes a data processing architecture to collect, classify, storage and analyze the data gathered by the topper, other external devices and the user interface, where the smart mattress topper system, through an Artificial Intelligence (AI) module, and using two main calculated indicators, specifically, the sleep quality and the aggregated recovery, and, when available, other secondary inputs, makes recommendations and when possible, acts over the own topper and other connected external devices in order to continuously improve user sleep quality and recovery level to face in the best optimal state, each day challenges.

9 Claims, 2 Drawing Sheets

(56) References Cited

U.S. PATENT DOCUMENTS

| | | | |
|---|---|---|---|
| 2017/0042471 A1* | 2/2017 | Meriheinä | A61B 5/4812 |
| 2019/0231083 A1 | 8/2019 | Hsu et al. | |
| 2021/0228942 A1* | 7/2021 | Erkkilä | G16H 50/20 |
| 2022/0176065 A1* | 6/2022 | Youngblood | G16H 40/40 |
| 2022/0249020 A1* | 8/2022 | Lizio | G16H 50/30 |
| 2022/0375590 A1* | 11/2022 | Kinnunen | A61B 5/742 |
| 2022/0375591 A1* | 11/2022 | Kinnunen | G16H 50/20 |
| 2022/0401689 A1* | 12/2022 | Campanella | A61M 21/00 |

FOREIGN PATENT DOCUMENTS

| | | | | |
|---|---|---|---|---|
| CN | 115422437 A * | 12/2022 | | A47C 27/15 |
| EP | 3527111 A1 | 8/2019 | | |
| ES | 2970110 T3 * | 5/2024 | | A47C 21/04 |

* cited by examiner

SMART MATTRESS TOPPER SYSTEM AND ASSOCIATED METHOD

OBJECT OF THE INVENTION

The present invention is related to the technical field of mattresses and other rest surfaces.

More specifically, it is related to mattresses and other rest surfaces that comprise means of controlling the user's rest and/or means of acting on the mattress or the rest surface, and/or on other external elements associated with the sleep environment and make recommendations to the user, in order to improve the parameters measured, mainly the Aggregated Recovery index, using among others the Sleep Quality Index.

BACKGROUND OF THE INVENTION

Sleep is a fundamental part of life since about ⅓ of our lives is spent sleeping. Although all the functions of sleep are not fully understood, sleep is recognized to be an active and dynamic process of physical and mental recovery. It is associated with growth, repair, and maintenance of body functions. It supports proper functioning of the immune system and it is also linked to the reorganization of the central nervous system networks. Sleep affects almost every type of tissue and body system from the brain to cardiovascular, pulmonary, metabolic/hormonal, and immune system activity and also affects heart rate and heart rate variability (HRV), respiratory rate, blood pressure, and body temperature.

Sleep has various substantial health effects, and an inadequate sleep and sleep deprivation may cause serious negative health consequences. Lack of sleep has been associated with weight gain and obesity, diabetes, hypertension, heart disease, stroke, depression, impaired immune function, increased pain, impaired performance, increased error rates during tasks, greater risk of accidents, and increased risk of death. Sleep affects learning and memory, cognitive performance, and alertness.

Sleep can be considered as recovery when falling asleep is easy, when sleep is continuous, when the person does not wake up too early, when waking is accompanied by feelings of being refreshed, and when daytime performance levels are not decreased. These elements, however, can be challenging to evaluate objectively as a whole, as some are definitively subjective in nature. Luckily it is well known that the autonomic nervous system (ANS) is a key regulatory system for the body, and that sleep is reflected in ANS activity. Generally, the parasympathetic branch of the ANS should be primarily dominant during sleep what reflects a relaxed state. A high sympathetic drive can be a sign of suboptimal recovery and physiological stress. The ANS state is also affected by different stages of sleep. Cardiovascular activity, for example, is very stable in the deep sleep, whereas, it can be highly variable during REM sleep, often reaching levels seen during wakefulness.

A well know method to evaluate autonomic nervous system (ANS) function uses HRV data. This allows for assessment of body stress and recovery states during sleep.

Sleep can be affected by various internal and external stressors. High levels of perceived stress, worries, and anxiety can make it difficult to fall asleep and to stay asleep. Too much daylight can disrupt and confuse the body's circadian regulation. Travel across time zones can similarly disturb the body's internal clock and disrupt sleep. Alcohol, other stimulating substances, and medications can markedly disturb sleep by affecting brain function, sleep structure, and autonomic nervous system activity. Regular physical activity may promote sleep, but disrupting homeostasis with strenuous physical activity can cause sympathetic overdrive in the ANS and negatively affect sleep, especially if performed too close to bedtime. Environmental factors (i.e., light, noise, $CO_2$ level, room temperature . . . ) and obviously an inappropriate sleep surface can also interfere our natural sleep.

Digging deeper in the past, it is well known the main ways in which a sleep surface can cause sleep disturbances: a) a surface that doesn't provide the right support to the different zones of the spine what will lead to pressure on the spinal nerves in the position in which they come out of the backbone; b) a surface that by its composition significantly increases the pressure applied on exposed body parts (hips, shoulders, etc.), which can lead to a disturbance in blood flow through capillaries, and as a result an insufficient oxygen and nutrient supply; c) a surface that due to the materials used in its construction favors the heat and humidity retention and therefore interferes with the natural temperature regulation of the body, temperature controlled by the circadian rhythms of the person and that is essential to favor the sleep onset due to selective vasodilation of distal skin regions but also a higher sleep efficiency; d) the human brain will not switch off when in a new and possibly dangerous environment; one half of our brain will not sleep as deeply as the other half (the so called First-Night-Effect) in an attempt to ensure survival. This happens when we constantly change our sleep surface (as we do when we travel) what leads to us feeling shattered the next morning.

In this regard, there are documents which belong to the state of the art that try to achieve a better control of the user's sleep parameters, by means of using different type of sensors to monitor them.

Document WO2019141904 refers to a method and apparatus for detecting stages of sleep of a person, by means of receiving temperature data and heart rate data of the user, and determining the temperature variability and the heart rate variability (HRV).

Document MX20180007224 refers to drowsiness onset detection implementations which predict the transitions of a person from a state of wakefulness to a state of drowsiness, based on the Heart Rate information, by means of heart rate sensors, monitoring the HRV signal to extract features that are indicative of an individual's transition from a wakeful state to a drowsy state. The system can also act to stimulate the person to a different state, or notify other people about this state.

KR20170099192, refers to a system for sensing a sleeping posture based on the internet of things (IoT), with respect to a bed which comprises a mattress with supports, and a frame under the said mattress, where the mattress comprises a sensor unit to sense the user sleeping condition, sending the results to an external mobile terminal comprising an application which compares the data received with the data reference, performing an analysis of this comparison.

KR20190026422 refers to a smart bed system with pressure sensors and an IoT controller for receiving the data from the pressure sensors, and outputting data about a posture pattern from a database, through a wireless network; a monitoring system for extracting the posture pattern, comparing the extracted posture pattern of the user in the bed, with the one extracted from the database, sending the information to a third person, like a caregiver or a nurse.

Finally, we can find the document WO2018073473, which refers to a method for improving quality of sleep, comprising the steps of measuring pressure by means of sensors in locations divided up by region of a mattress; calculating the SQI from the main movements detected at different times of the night; calculating the mean pressure measured by each sensor; calculating the difference between the mean pressure and the pressure measured by that sensor when there is no user on the mattress; calculating the mean difference in pressure for each region of the mattress; calculating a weight factor for each region of the mattress; comparing the weight factor with a reference value; varying the configuration of the mattress by increasing or reducing the level of support in the different regions. A related system and mattress are also disclosed.

These documents include different systems to measure sleeping parameters of the user, like temperature or heart rate, calculating the stage of sleep of the same, and the transitions between the said stages of sleep. They also include pressure sensors to measure the pressure in different points of the mattress, which are distributed through the complete area.

With these parameters, the systems belonging to the state of the art can calculate the SQI and, using IoT connections by means of wireless communications, transfer the information to external devices, like smartphones or similar.

However, these documents are not able to connect the data obtained by the sensors with an algorithm, which can use this information or another information from other users, to act over the mattress in real time, and act directly over the different elements included in the mattress or indirectly over other external elements that can control the environmental conditions, and to make recommendations to the user in order to improve the resting time during the sleep and the associated recovery.

SUMMARY OF THE INVENTION

The smart mattress topper system and the associated method that the invention proposes are configured, therefore, as a remarkable novelty within its field of application, since according to its implementation and in an exhaustive manner, the aforementioned objectives are satisfactorily achieved, with the characterizing details that make it possible and that distinguish them are conveniently collected in the final claims that accompany this description.

Particularly, this invention describes a method that uses a smart mattress topper connected to the Internet (IoT), which includes a data processing architecture to collect, classify, store and analyze the data gathered by the topper, other external devices and the user interface, where said method, through an Artificial Intelligence (AI) module using the aggregated recovery index (ARI), and when available other secondary inputs, such as activity, physiological indicators such as distal skin temperature, environmental ones such as room temperature, biomarkers such as CPK, lifestyle related ones such as diet, etc., makes recommendations in order to continuously improve user sleep quality and recovery level to face in the best optimal state, each day challenges.

Additionally, the system is able to actively act over the own topper and other connected external devices.

With this mattress topper system, it is introduced a continuous improvement in the user sleep quality and recovery level, learning with the application of algorithms by means of the AI.

In order to achieve the aforementioned objectives, the mattress topper comprises a plurality of variable pressure elements, a Ballistocardiograph sensor, BCG from now on, and a control box with a control unit and wireless and/or wired connection means to other external elements.

In a first place, the plurality of variable pressure elements comprises pressure sensors, where these sensors perform measurements about the pressure exercised by the user when laying on the bed, and where the support level of the variable pressure element can be changed by different means, to adapt to the morphology of the user, in response to the pressure measurements of the sensors, providing him or her the right support to the different areas of the body.

For example, the variable pressure elements can be small air bladders, where the support level can be adjusted by allowing more or less air inside them.

In a second place, the BCG sensor is in charge of producing a graphical representation of the repetitive motions of the human body, arising from sudden ejection of blood into the great vessels, with each heartbeat.

Finally, the control box includes a control unit, operatively connected to the rest of the elements that the mattress topper comprises, and connection means to other external elements, that can provide more information about the sleeping parameters of the user, like the heart rate, the respiration rate, the movement, the stroke volume, or any other parameters.

With the information obtained from the external devices, the sensors of the variable pressure elements and the BCG sensor, the control unit is capable of commanding the variable pressure elements, and to process different algorithms, obtaining more information such as the heart rate variability (HRV) or the sleep quality.

Also, the mattress topper, either through the control box described above or through the BCG sensor, includes the possibility to receive user data in real time from associated trackers, to measure other physiological indicators, such as skin temperature, peripheral capillary oxygen saturation (SPO2) level, blood pressure or Electrodermal Activity (EDA).

With all these elements, including the different measurements, the variable pressure elements and the control box, the system is capable to act over the mattress topper, controlling the sleeping parameters of the user, with more accurate information about sleep phases, indications of the best time to go to bed, and improve recovery level metrics, or even predict some external event, such as migraine crises or epilepsy seizures, to name a few.

The information obtained is used to monitor or influence over the autonomic nervous system (ANS), which is assessed using beat-to-beat heart rate data, and provides two types of states: the parasympathetic or the sympathetic.

When parasympathetic modulation is dominant, heart rate (HR) is individually low and heart rate variability (HRV) high. This is detected and described as a recovery/relaxation state.

When sympathetic modulation predominates, HR elevates and HRV generally declines from the individual's baseline levels. This is detected as a stress state by the analysis. The stronger the parasympathetic or sympathetic modulation, the stronger the relaxation or stress intensity, respectively.

It is known that during wakefulness parasympathetic activity decreases and/or sympathetic activity increases. Conversely, during sleep, parasympathetic modulation should predominate to ensure body restitution. The deeper the sleep is, the stronger the parasympathetic modulation is. However, bursts of sympathetic activity occur during restless periods or awakenings during sleep.

Another technical characteristic of the invention is its capability to connect to other control elements by means of using IoT networks. This network can be used to collect external information and command other external devices, that control mainly the environment of the room where the smart mattress topper system is located, like the temperature, the humidity, the darkness level, or the $CO_2$ level.

This interaction, as explained above, is performed by means of an IoT connection, preferably at cloud level through the Application programming interface (API).

It has been demonstrated that all the mentioned parameters have serious impact on sleep quality and on recovery, so having a smart mattress topper system that can centralize all this information, and controlling it from a holistic perspective, gives the invention a great advantage.

The smart mattress topper can be made of low resilient materials, such as memory foam, in order to reduce the pressure points over the body of the user. A material with increased thermal conductivity and/or ventilation properties can be used, in order to increase conductivity of the body heat loss. This reduces the core body temperature.

Additionally, the smart mattress topper system can comprise other elements to improve the temperature regulation of the user, decreasing the temperature of the smart mattress or increasing it in a particular zone, such as Peltier coolers or thermoelectric coolers (TECs).

These additional elements can be attached to an external element, such a grid, to disseminate water or air inside the mattress to make such temperature regulation.

With these two characteristics, the elements used to improve the temperature regulation can be directly attached to the mattress topper, or they can be located in an external mean, that can increase or decrease the temperature of a fluid, in communication with the mattress topper, performing an indirect temperature regulation of the same.

In another aspect, the mattress topper object of the present invention is a portable element, that can be taken when travelling, and is adaptable to any location, in order to convert an unknown sleeping surface in a known one where the First-Night-Effect can be reduced and therefore sleep quality can be improved, what is an important advantage over the state of the art smart mattresses that are not portable.

The mattress topper of the invention may include other functionalities with the same aim of improving recovery through sleep. It has been also shown by research, that compression on certain trigger points increases parasympathetic nervous activity based on heart rate variability favoring sleep and therefore recovery.

The mattress topper, in its preferred configuration, by the inflation and deflation of the variable pressure elements is able to exercise a massage function through gentle pressure and then releasing the muscles and blood vessels. The skin and muscles contain huge nerve connections and therefore, the gentle massage by nerves causes the relief and recovery of health in any part of the body. Massage therapy is a well-known method to improve sleep disorders and also to increase blood circulation, it relieves stress, helps the digestive system and its performance, stimulates the lymphatic system, improves the function of the autonomic nervous system, decreases heart rate and blood pressure, causes the secretion of endorphins and thus reduces back pain, insomnia and calms the patients.

Furthermore, the mattress topper can include some extra vibration elements such as haptic actuators that could be used as a complement to the massage function but also as a way to alert the user on certain bad postures while laid down or sit on the topper and any other alert such as a gentle wake up alarm, indication on set up process, etc.

With a similar objective, the mattress topper can include speakers to reproduce Solfeggio Frequencies, binaural beats or any other sound wave therapy to favor the relaxation function, reducing stress level and shortening the latency time.

Also the mattress topper can include PEMF therapy, which sends magnetic energy into the body. These energy waves work with the body's natural magnetic field to improve healing. The magnetic fields help to increase electrolytes and ions. This naturally influences electrical changes on a cellular level and influences cellular metabolism. It works with the body's own recovery processes.

Regarding these last characteristics, the control unit of the control box will be in charge of controlling them, that is, the inclusion of the active thermoregulation system, the vibration elements, the speakers sound therapy and the PEMF therapy, according to the information received from the pressure sensors, the BCG or the external devices connected; and also based on the application of the AI algorithms.

Finally, the smart mattress topper system will use a user interface, where the information is easily visualized by the user, and also permits the input data from other related platforms, such Apple Health or google Fit, at cloud level, as explained before.

The present invention also describes the operation procedure of the smart mattress topper system described above, that starts from the data obtained from: the sensors included in the mattress topper, the external devices, external environment factors, and the subjective inputs requested to the user by means of the user interface.

This procedure begins with extraction of the information from the sensors installed in the mattress topper, in combination with the external devices. This obtained data is processed in order to extract, transform and filter it, by means of techniques and methods based on AI and Data science, intending to control the pressure of the variable pressure elements and the environment where the mattress is located, and also gives recommendations to the user, based on the factors that depend on the user behavior.

The information analysis begins with the calculation of two key indicators, the Sleep Quality Index (SQI) and the Aggregated Recovery Index (ARI).

Additionally, other indicators can be very valuable to give more information about the specific situations, such as, for example, the thermoregulation, heavily related with the sleep, since the core body temperature decreases, due to the increase of peripheral skin temperature, associated with the melatonin secretion. Other inputs might come from the external environment factors, such as the room temperature, darkness level, $CO_2$ level or humidity.

All this information will help the algorithm used by the control unit to understand the deviations from sleep and recovery from the ideal situation, and also make the aforementioned recommendations to the user.

Finally, there are the subjective inputs that are requested to the user from the user interface, such the feeling when wake up or the stress level of the day. Typically, this interface will be supported in a smart device, such a smart phone, a tablet or similar.

To perform all the operations described, which go from the initial measurements of the sensors, to the control of the mattress, the control of the environment factors, and the recommendations given to the user, the control unit comprises the next modules: an information retrieval module, receiving the information; the information processing module, in charge of carrying out the processing of the information received; the knowledge generation module, which stores the information, generating a data base; and the artificial intelligence module, which performs the analysis of the information received, in combination with the subjective information from the user, supporting the dynamic analysis of large data flows.

With the characteristics above, the smart mattress topper system measures, collects and distributes the information, but the relevant technical characteristic remains in this last module, as far as the AI is capable of learning from the information and experiences of the user and other users, and is capable of making recommendations on the mattress topper settings, external devices settings and any other related with the user's lifestyle.

In parallel to the previous modules, the AI module uses the next algorithms to achieve the aforementioned objectives: a Day Zero Model, in charge about the initial settings and recommendations given to the new user; the Intra-User Model, which is in charge of the explanation and the recommendations; and the Inter-User Model, that supports the Intra-User Model when it is not enough.

The smart mattress topper system and the associated method and the set of elements described represent an innovation with hitherto unknown structural and constitutive characteristics, reasons that, together with its practical utility, provide it with sufficient grounds to obtain the requested exclusivity privilege.

BRIEF DESCRIPTION OF THE DRAWINGS

To complement the description that is being made and in order to help better understand the features of the invention, a set of drawings in which the following is depicted in an illustrative and non-limiting character is attached as an integral part of said description.

PREFERRED EMBODIMENTS OF THE INVENTION

Figure 1:
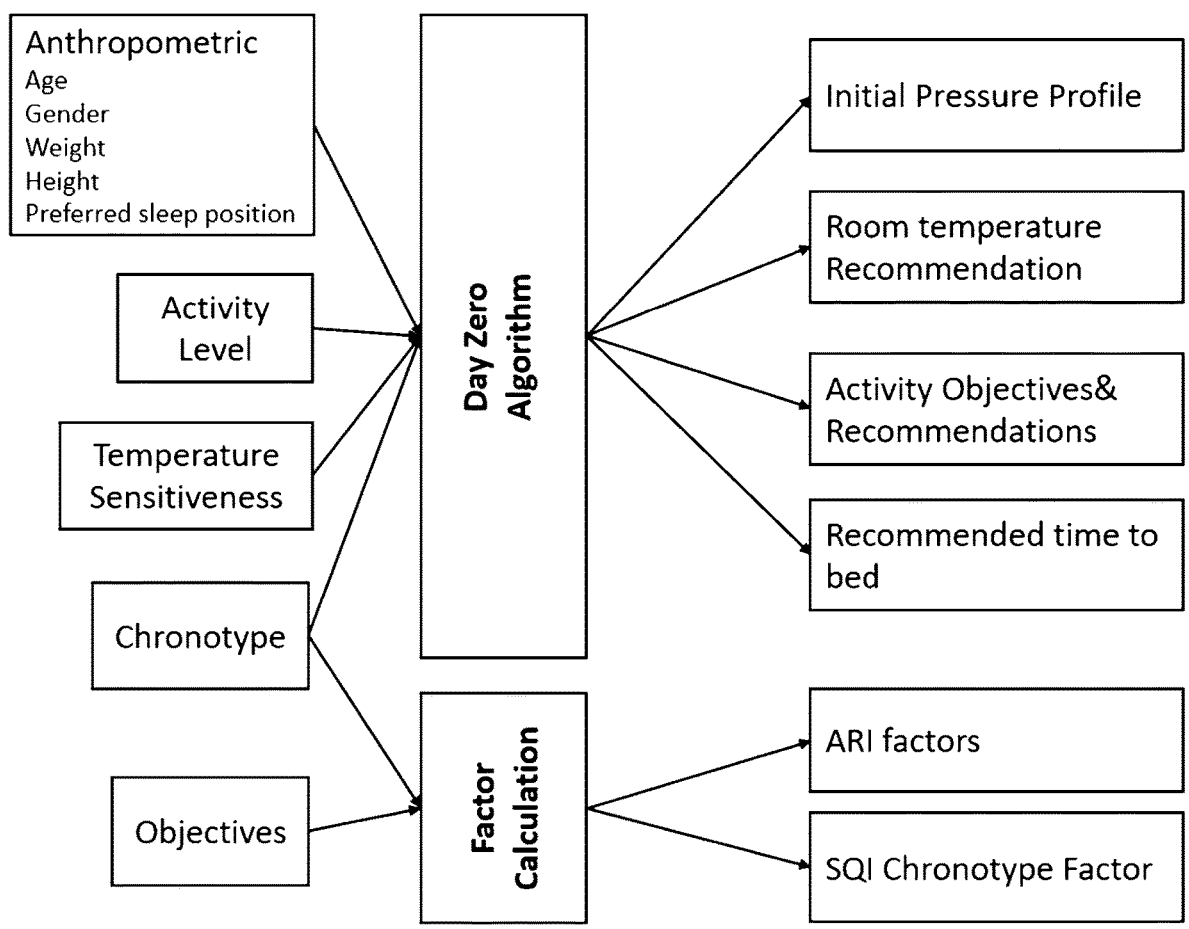
FIG. 1.—Initial set up of the smart mattress topper system by means of the Zero Day algorithm and the Factor Calculation.

In the following detailed description of the preferred embodiments, reference is made to the accompanying drawings which form a part hereof, and in which there are shown by way of illustration specific preferred embodiments in which the invention may be practiced. These embodiments are described in sufficient detail to enable those skilled in the art to practice the invention, and it is understood that other embodiments may be used and logical structural, mechanical, electrical, and/or chemical changes may be made without departing from the scope of the invention. To avoid details not necessary to enable those skilled in the art to carry out the detailed description should therefore not be taken in a limiting sense.

Particularly, the present invention describes a smart mattress topper system which comprises:
- a plurality of variable pressure elements, configuring the support layer of the smart mattress topper, with at least one pressure sensor in each variable pressure element;
- a BCG sensor, with wireless connection, configured to measure the sleeping parameters of the user, preferably the user heart rate, the breath rate, the HRV and the stroke volume;
- and a control box, which comprises a data storage means and a control unit, operatively connected to the other elements.

Where the control unit is configured to collect the information received from the pressure sensors and/or the BCG sensor, store the information in the data storage means; and process the information.

And where the variable pressure elements are configured to modify the occupied volume and/or the pressure exerted on the user lying on the smart mattress topper, in response to the measurements made by the pressure sensors by means of the control unit.

With this first embodiment of the present invention, the invention describes a smart mattress topper system that receives information from the BCG sensor and the pressure sensors, and can act over the variable pressure elements and give recommendations to the user based on the received information, to improve the sleeping quality and the recovery.

In a preferred embodiment, the control unit will perform a processing of the received information to calculate the Sleep Quality Index and the Aggregated Recovery Index.

Where the SQI will be numerically evaluated, from 0 to 100, with basis on:
- the movements of the user, received through the pressure sensors of the variable pressure elements;
- the latency, understood as the time that it takes for the user to fall asleep;
- the time out of bed, obtained when the pressure sensors are not detecting any reading;
- and the session time, understood as the time that the person remains asleep.

And where the ARI is the built-up aggregated score, that weights several indicators related mainly with sleep and vital signs.

In this case, the ARI calculation comprises the next 9 indicators:
- the last night SQI, as described above;
- the balanced SQI, comparing the last night SQI with the SQI trend;
- the deep sleep indicator, that is, the amount of time in which the user is in deep sleep, in comparison with the ideal.
- the last night HRV, that is, the variation in the time interval between consecutive heartbeats;
- the balanced HRV, that is, the last night HRV in comparison with the user trend;
- the rest heart rate, which compares the current heart rate with the average heart rate, in order to determine the relaxation level;
- the balanced rest heart rate, in comparison with the user's trend;
- the previous day activity level, when it is known;
- and the balanced activity level.

Where all these indicators are weighted with some correction factors, to give each one a predetermined relevancy in the ARI calculation.

In a preferred embodiment, the processing of the information, in addition to the calculation of the SQI and the ARI, will use AI algorithms, that are capable of learning from the information and the user experience, even other user experiences, in order to make recommendations to the user, for example about the user's lifestyle, and/or act over the mattress topper settings, other external devices or the environment control devices.

In order to perform this last characteristic, in a preferred embodiment, the invention will include a wireless connection by means of internet and/or Bluetooth and/or an IoT network, to allow the smart mattress topper to interact with external devices connected to the internet, allowing it to receive and send information to said external devices. With this connection, the smart mattress topper system will control directly the external devices.

Additionally, with the internet connection, the smart mattress topper system could connect to the cloud, interacting with different external elements, connected indirectly through the said cloud.

In another preferred embodiment, by means of using the IoT connection, the invention can connect with the environment control devices of the room where the smart mattress topper system is located, in order to act over them, controlling the environmental parameters of said room.

This is possible because the processing of the information received by the smart mattress topper system from the pressure sensors, the BCG sensor and other external devices; by means of using the AI algorithms.

In another preferred embodiment, the smart mattress topper system will include a wireless connection, such as Bluetooth, Wi-Fi, 5G, or similar, to an external smart device, such as a mobile phone or a tablet, by means of a user interface or an application installed in said external smart device, so the user can introduce manually data in the system and/or send it through other common applications installed in the external smart device.

This connection can be also performed using connection to the cloud, in which the mattress topper exchanges information with the external smart device.

Preferably, the smart mattress topper is made in a low resilient material such as memory foam, soft foam, or fibers; to reduce pressure points over the more sensitive body parts of the user, such as hips and shoulders, but at the same time has increased conductivity properties and/or air ventilation ones so it increases conductive body heat loss, reducing the core body temperature and increasing the deep sleep.

In a preferred embodiment, the smart mattress topper system can include at least one active element, acting as a thermoregulator, such as Peltier coolers or thermoelectric coolers, in order to regulate the working temperature of the mattress topper, helping the user in the recovery.

In a preferred embodiment, the active elements are located in an external device with a fluid in direct connection with the mattress topper, in order to regulate the temperature in said fluid.

With this preferred embodiment, the temperature regulation of the mattress topper is performed indirectly by the active elements, that is, firstly is increased or decreased the temperature of the circulating fluid, which subsequently goes into the mattress topper, being cooled or heated by means of the heat transfer performed by the fluid.

In another preferred embodiment, the active elements are located within the mattress topper, configured to regulate directly the working temperature of the same.

With this another preferred embodiment, the temperature regulation of the mattress topper is performed directly by the active elements.

In another preferred embodiment, the variable pressure elements include a massage mode that follows those recommendations of the AI algorithms, in order to trigger specific pressure points on the body to increase parasympathetic nervous activity based on heart rate variability, favoring sleep and therefore recovery.

In a preferred embodiment, the mattress topper can include at least one vibration element, that could be used as a complement to the massage function, and also as a way to alert the user on certain bad postures while laid or sit on the topper and any other alert such as a gentle wake up alarm, indication on set up process, etc.

In another preferred embodiment, the mattress topper can include at least one speaker to reproduce Solfeggio Frequencies, binaural beats or any other sound wave therapy to favor the relaxation function, reducing stress level and shortening the latency time.

In another preferred embodiment, the mattress topper can include means of generating electromagnetic fields, configured to perform a Pulsed Electromagnetic Field Therapy, which sends magnetic energy into the body.

In a preferred embodiment, the control unit of the mattress topper is in charge of controlling the vibration elements and/or the speakers and/or the means of generating the electromagnetic fields.

Regarding this last embodiment, the control unit act sover these means or elements according to the information received from the pressure sensors, the BCG sensor or the external devices connected.

It also acts over them with basis on the application of the AI algorithms, performing different recommendations to the user about the use of the vibration system, the emission of determined sounds by means of the speakers or the activation of the magnetic fields.

These means or elements are configured as an extra help to the user in order to increase the recovery and improve the sleeping experience.

In a preferred embodiment, the architecture of the control unit comprises at least:
- an information retrieval module, configured to carrying out the receiving of the information from the different resources;
- an information processing module, configured to carrying out the processing of the information received in the previous module;
- a knowledge generation module, configured to storing the extracted and processed information;
- an artificial intelligence module, configured to apply the AI algorithms.

Finally, in the last preferred embodiment, the smart mattress topper comprises a folding system, with a previous compression system, configured to allow the user to transport it to different locations, that is, the folding system allows the mattress topper to be portable.

On the other hand, the present invention also describes the operating method associated to the smart mattress topper system, which comprises at least the next steps:
- collection of the user's information through the pressure sensors of the variable pressure elements and/or the BCG sensor;
- storage of the collected information in the data storage means and/or the cloud by means of IoT;
- calculation of the Sleep Quality Index and the Aggregated Recovery Index;
- processing of the information by means of AI algorithms;
- actuation over the pressure exerted on the user lying on the smart mattress or sending of recommendations to the user and/or control of the environment parameters.

With this procedure, the smart mattress topper system obtains the information from the pressure sensors and the BCG sensor, stores it and makes the referenced calculations in order to obtain the SQI and the ARI, that are transferred to the artificial intelligence module in order to apply the AI algorithms, obtaining the needed information to act over the smart mattress topper or the devices that control the environment parameters, and sends recommendations to the user.

In a preferred realization of the method, the information can be obtained from the external devices and/or the information introduced by the user through the user interface, using them in combination with the ones coming from the pressure sensors and the BCG sensor, to give more accurate information to the Artificial Intelligence module.

The algorithms that the Artificial Intelligence module applies are comprised by, at least, one of the next algorithms: the Zero-day model, the Intra-user model and the Inter-user model.

Where the Zero-day model is a prediction model, configured to set the initial settings of the smart mattress topper system and/or other connected devices; and/or give initial recommendations to the user, by means of the initial information received from the user interface.

This Zero-day algorithm, as it can be observed in the FIG. 1, is performed only the first time the users need to set up the smart mattress topper system. In this case, by means of introducing the personal data in the same, such as the anthropometric data, like age, gender, weight, height or the preferred sleep position; it is also introduced the activity level, the temperature sensitiveness or the chronotype.

The initial set up is completed by the calculation of the ARI factors and the Chronotype factor of the SQI based on the performance objectives and the chronotype of the person.

With all these data, the Zero Day algorithm calculates different initial set up parameters, like the initial pressure setting of the support surface, the room temperature recommendation, the activity objectives and recommendations, or the recommended time to go to bed.

Where the Intra-user model algorithm acts after the first day of use and is configured to give recommendations to the user about the factors to change, when there is a deviation from the Aggregated Recovery Index calculated.

And where the Inter-user model algorithm that acts also after the first day of use, is configured to give recommendations to the user, in the basis of other user experience, when there have not been changes in the user, such as a maintained or increasing ARI; in the settings of the smart mattress topper system and/or in the environmental conditions.

To explain when the Intra user or the Inter user algorithms apply, the smart mattress topper system uses a decision tree, which is explained below.

In this case, with the beginning, the smart mattress topper system calculates the ARI variation, attending on the previous data storage in the cloud.

If the ARI has not decreased, that is, the ARI has no variation or has increased, the Inter-user algorithm makes a recommendation analysis, to improve the ARI, in basis on the recommendations made previously to other users or other recommendations made to the same user, with an expectation of percentage of improvement.

If the ARI has decreased, the Intra-user algorithm analyzes the possible causes, within the 9 factors included in the ARI calculation, trying to know if there has been a change in the SQL In the affirmative case, the Intra-user algorithm determines the cause, within the different parameters, such as the time awake, the latency, the movements or the sleeping time.

If the cause is the sleeping time, the recommendation will be directed to the time to go to bed, with an expectation of percentage of improvement.

In the case the sleeping time is not the cause of the ARI decrease, the smart mattress topper system will analyze if it is related with any other subjective information, like drinking of coffee or activity level of the day.

If there is any subjective information related with the ARI decrease, both the Intra-user and the Inter-user, will perform recommendations on the subjective behaviors, with an expectation of percentage of improvement.

If there is no subjective information related with the ARI decrease, the smart mattress topper system will make recommendations to change the support level of the element that compose the support layer.

On the contrary, when the ARI decrease is not because a change in the SQI, the smart mattress topper system will check if there is any subjective information, such as a change in the user objective, or other external ones, that could affect the ARI of the user, making recommendations to the user, by means of both algorithms, the Intra-user and the Inter-user.

Figure 2:
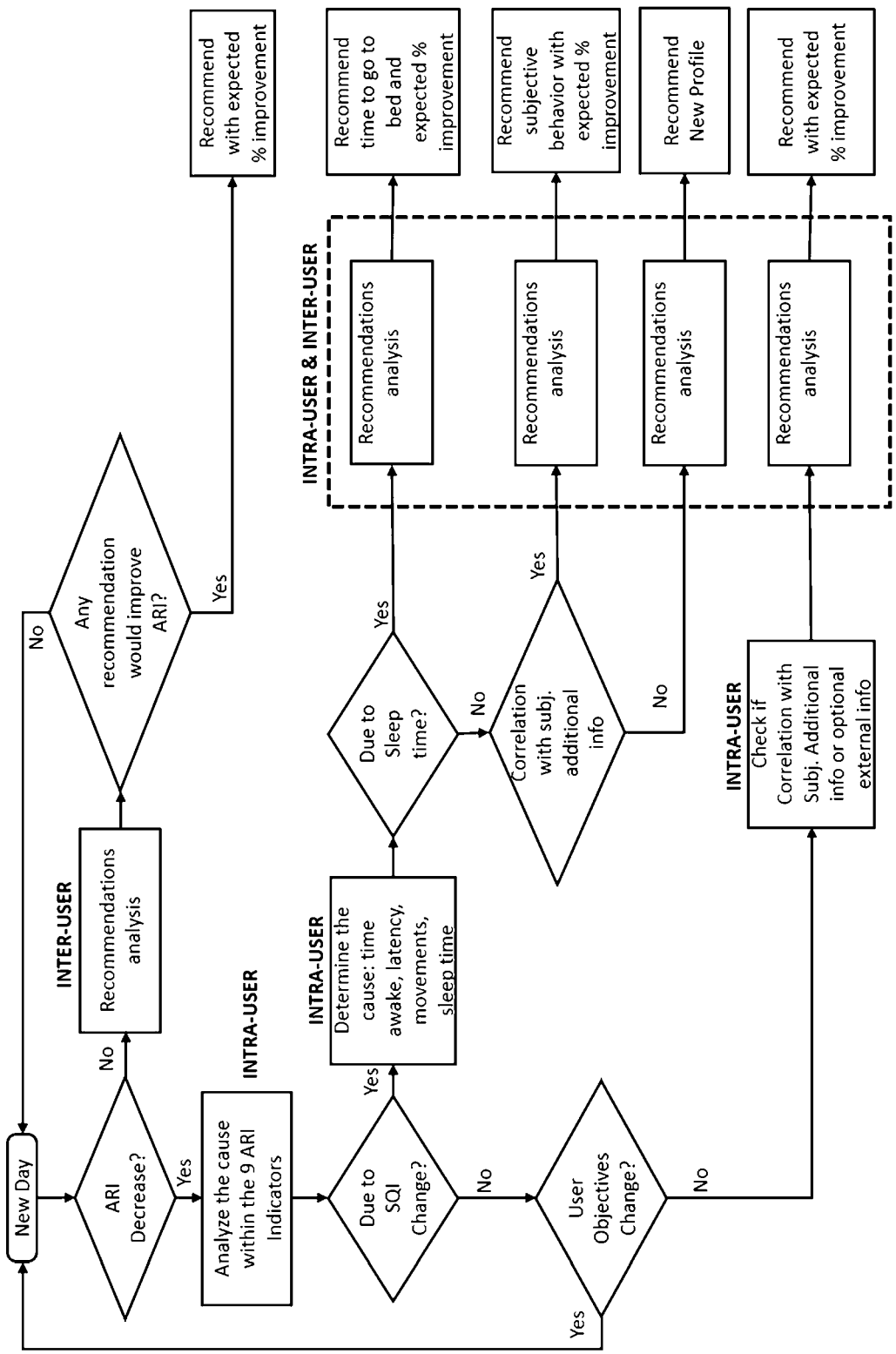
FIG. 2.—Decision tree of the smart mattress topper system, to decide when to apply the different algorithms.

With this decision tree, working as shown in the FIG. 2, the smart mattress topper system will analyze first the ARI variation, to decide the algorithm to be used in each case, that is, the Inter-user or the Intra-user algorithms.

And, in the case that there is an ARI decrease, the smart mattress topper system will use the other information from the user to perform the recommendations, such as the SQI, the sleeping time or the subjective information.

With this decision tree, in combination with the three defined algorithms, the smart mattress topper system is capable of performing different recommendations to the user every day, depending on the information received and the variations of the ARI.

The smart mattress topper system also can perform the activation of the active elements that act as thermoregulators, in response to a signal sent by the control unit, based on the information received and the information processed with the AI algorithms.

In a preferred method, according to the embodiment that includes the vibration elements or the speakers or the means of generating an electromagnetic field, it comprises the activation of any of these elements according to the information received from the pressure sensors, the BCG sensor, the external devices connected or the information processed by the AI algorithms.

Regarding the AI algorithms, the recommendations performed in the different models can include recommendations about the using of the vibration elements, the emission of determined sounds through the speakers or the activation of the electromagnetic field to perform a PEMF therapy.

The previous implementations can also be included in a common mattress, since this fulfills the same functions, or very similar ones, to those fulfilled by a common mattress topper. That is, the invention can be included in a smart mattress. Accordingly, within the meaning of the subject invention, by mattress topper it shall also be understood any mattress or any other sleeping device or rest surface.

Having sufficiently described the nature of the present invention, as well as the way of putting it into practice, it is not considered necessary to make its explanation more extensive so that any person skilled in the art understands its scope and the advantages derived from it, stating that, within its essentiality, it may be put into practice in other forms of embodiment that differ in detail from the one indicated by way of example, and to which it will also achieve the protection that is sought as long as its fundamental principle is not altered, changed or modified.

The invention claimed is:

1. A method associated to a smart mattress topper system comprising:
    collecting the user's information through pressure sensors of the variable pressure elements and a BCG sensor;
    storing the collected information in a data storage means and/or the cloud by means of IoT;
        calculating the Sleep Quality Index and the Aggregated Recovery Index;
        processing the information by means of AI algorithms; and
        actuating over the pressure exerted on the user lying on the smart mattress or
    sending of recommendations to the user and/or control of the environment parameters, wherein the AI algorithms are at least, one of the algorithms selected from the group consisting of Zero-day, Intra-user model and Inter-user model.

2. The method associated to the smart mattress topper system according to claim 1, further comprising collecting the user's information through a connection with external devices, or through a user interface.

3. The method associated to the smart mattress topper system according to claim 1, characterized in that the Zero-day algorithm is a prediction model, configured to set the initial settings of the smart mattress topper system and/or other connected devices; and/or give initial recommendations to the user, by means of the initial information received from the user interface.

4. The method associated to the smart mattress topper system according to claim 1, characterized in that the Intra-user model algorithm is configured to give recommendations to the user about the factors to change, when there is a deviation from the Aggregated Recovery Index calculated.

5. The method associated to the smart mattress topper system according to claim 1, characterized in that the Inter-user model algorithm is configured to give recommendations to the user, in the basis of other user experience, when there have not been changes in the user, the settings of the smart mattress topper system and/or the environmental conditions.

6. The method associated to the smart mattress topper system according to claim 1, characterized in that the method uses a decision tree in order to decide when apply the different algorithms, said method further comprising, at least, the next steps, beginning with the calculation of the ARI variation:
    if there is not a decrease in the ARI variation, the Inter-user algorithm makes recommendations to the user in order to improve the ARI;
    if there is a decrease in the ARI variation, the smart mattress topper system analyzes the possible causes of the decrease within the factors included in the ARI calculation, and analyzes if there is a change in the SQI:
        i. if there is a change in the SQI, the Intra-user algorithm determines the cause and gives recommendations to the user
        ii. if there is not a change in the SQI, the smart mattress topper system checks if there is any subjective information and/or another external information, that can affect the ARI of the user, making recommendations to the user by means of the Intra-user algorithm and the Inter-user algorithm.

7. The method associated to the smart mattress topper system according to claim 1, further comprising activating thermoregulators in response to a signal sent by a control unit, based on the information received and the information processed with the AI algorithms.

8. The method associated to the smart mattress topper system according to claim 1, further comprising activating vibration elements and/or speakers and/or means of generating an electromagnetic field.

9. The method associated to the smart mattress topper according to claim 1, characterized in that the recommendations performed by the AI algorithms include the activation of vibration elements and/or speakers and/or means of generating an electromagnetic field.

* * * * *